United States Patent [19]
Loev

[11] 3,948,892
[45] Apr. 6, 1976

[54] 2-ALKOXY(AND 2-AMINO)-3-AMINO-2-HETEROCYCLIC-THIOPROPANAMIDES
[75] Inventor: Bernard Loev, Broomall, Pa.
[73] Assignee: SmithKline Corporation, Philadelphia, Pa.
[22] Filed: Oct. 15, 1974
[21] Appl. No.: 514,684

Related U.S. Application Data
[62] Division of Ser. No. 322,572, Jan. 10, 1973, Pat. No. 3,860,592.

[52] U.S. Cl. 260/247.1 M; 260/250 BN; 260/256.5 R
[51] Int. Cl.² .............. C07D 237/08; C07D 239/26
[58] Field of Search 260/247.1 M, 250 BN, 256.5 R

[56] References Cited
UNITED STATES PATENTS
3,740,409  6/1973  Brenner et al. .................... 260/250
3,749,728  7/1973  Loev .................................. 260/250

Primary Examiner—James A. Patten
Assistant Examiner—Michael Shippen
Attorney, Agent, or Firm—Joan S. Keps; Richard D. Foggio; William H. Edgerton

[57] ABSTRACT

The compounds are 2-alkoxy(and 2-amino)-3-amino-2-heterocyclic-thiopropanamides, for example 2-methoxy-N-methyl-3-morpholino-2-(2-pyridyl)thiopropanamide, which are inhibitors of gastric acid secretion.

6 Claims, No Drawings

2-ALKOXY(AND 2-AMINO)-3-AMINO-2-HETEROCYCLIC-THIO-PROPANAMIDES

This is a division of application Ser. No. 322,572 filed Jan. 10, 1973 now U.S. Pat. No. 3,860,592.

This invention relates to new 2-alkoxy(and 2-amino)-3-amino-2-heterocyclic-thiopropanamides having pharmacological activity. In particular, these compounds inhibit gastric acid secretion.

The compounds of this invention are represented by the following formula:

FORMULA I

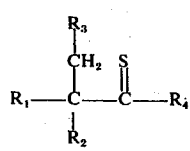

in which:

$R_1$ is 2-pyridyl, 2-pyrimidyl, 4-pyrimidyl, 2-pyrazinyl, 2-pyrrolyl, 2-quinolyl, 2-thiazolyl or 4-thiazolyl;

$R_2$ is lower alkoxy, allyloxy, cyclopropanemethoxy, di-lower alkylamino, piperidino, pyrrolidino, N-lower alkylpiperazino or morpholino;

$R_3$ is di-lower alkylamino, piperidino, pyrrolidino, N-lower alkylpiperazino or morpholino;

$R_4$ is NH-(lower alkyl), N(lower alkyl)$_2$, NH-phenyl, NH-$(CH_2)_n$-cycloalkyl, said cycloalkyl having 3–6 carbon atoms, or NH-$R_5$;

$n$ is 0 or 1 and $R_5$ is allyl or propargyl optionally substituted by methyl or ethyl groups, said $R_5$ having 3–6 carbon atoms.

This invention also includes pharmaceutically acceptable acid addition salts of the compounds of Formula I.

The pharmacologically active compounds of this invention have the basic structure of Formula I. However, it is apparent to one skilled in the art that well known nuclear substituents such as lower alkyl, lower alkoxy or halogen may be incorporated on the heterocyclic rings. These substituted compounds are used as are the parent compounds.

In the compounds of Formula I, preferably $R_3$ is morpholino. Also, preferably $R_1$ is 2-pyridyl. $R_2$ is preferably lower alkoxy.

Preferred compounds of this invention are represented by Formula I in which $R_1$ is 2-pyridyl, $R_2$ is methoxy, $R_3$ is morpholino and $R_4$ is NH-methyl, NH-ethyl, NH—$(CH_2)_n$-cycloalkyl or NH-allyl.

A particularly advantageous compound of this invention is 2-methoxy-N-methyl-3-morpholino-2-(2-pyridyl)-thiopropanamide.

The compounds of this invention produce inhibition of gastric acid secretion. This activity is demonstrated by administration to pylorus ligated rats at doses of about 10 mg./kg. to about 50 mg./kg. orally. In this procedure, compounds which produce an increase in gastric pH or a decrease in the volume of gastric juice or both are considered active.

These compounds show antiulcer activity, for example in the restraint-stress method in which an oral administration to rats these compounds inhibit the development of experimental ulcers.

The compounds of this invention are prepared by the following procedures:

I.

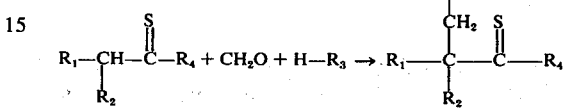

The terms $R_1$–$R_4$ are as defined above.

According to procedure I, a 2-alkoxy(or 2-amino)-2-heterocyclic-thioacetamide is reacted with formaldehyde and an amine. The reaction is preferably carried out by reacting the thioamide with a slight excess of formaldehyde and amine in alcoholic solution, preferably at elevated temperature, for example at reflux temperature.

II.

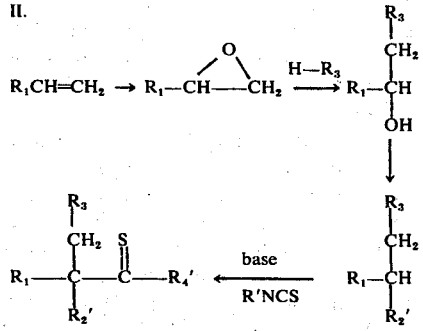

The terms $R_1$ and $R_3$ are as defined above; $R_2'$ is lower alkoxy, allyloxy or cyclopropanemethoxy; $R'$ is lower alkyl, phenyl, $(CH_2)_n$-cycloalkyl or $R_5$; $R_4'$ is NH-(lower alkyl), NH-phenyl, NH-$(CH_2)_n$-cycloalkyl or NH-$R_5$; and $n$ and $R_5$ are as defined above.

According to procedure II, the vinyl group of a vinyl heterocycle is oxidized to the ethylene oxide ring and the resulting compound is reacted with an amine to give a 2-heterocyclic-2-hydroxylamine. The hydroxy group is converted to an ether ($R_2'$) by standard procedures and the resulting 2-alkoxy compound is reacted with a strong base such as phenyl or butyl lithium and then with an appropriate isothiocyanate to give N-substituted 2-alkoxy-3-amino-2-heterocyclic-thiopropanamides of this invention.

The thioacetamide starting materials in the above procedure are prepared by the following procedures:

A.

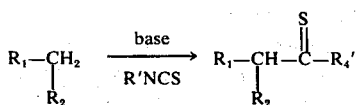

B.

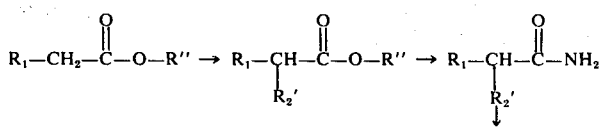

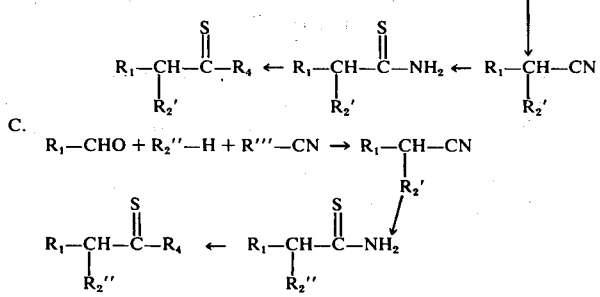

C.

The terms $R_1$, $R_2$, $R_4$, $R'$, $R_2'$ and $R_4'$ are as defined above; $R''$ is lower alkyl, preferably methyl or ethyl; $R'''$ is an alkali metal; and $R_2''$ is di-lower alkylamino, piperidino, pyrrolidino, N-lower alkylpiperazino or morpholino.

According to procedure A, an alkoxymethyl or aminomethyl heterocycle is reacted with a strong base such as phenyl or butyl lithium and then with an appropriate isothiocyanate to give the N-substituted 2-alkoxy(and 2-amino)-2-heterocyclic-thioacetamides.

The alkoxymethyl-heterocycles are prepared by reacting a halomethyl-heterocycle with an alkoxide, such as sodium alkoxide, or alternatively, by reacting a heterocyclic-methanol with an appropriate halide, for example a lower alkyl, allyl or cyclopropanemethyl chloride or bromide, in the presence of a base such as sodium hydride.

According to procedure B, a lower alkyl 2-heterocyclic-acetate is converted to the 2-alkoxy compound by reacting with N-bromo or N-chlorosuccinimide and reacting the resulting 2-bromo or 2-chloro compound with a sodium alkoxide; the resulting lower alkyl 2-alkoxy-2-heterocyclic-acetate is converted to the corresponding acetamide by reacting with ammonium hydroxide; the acetamide is dehydrated to give the corresponding nitrile and the nitrile is converted to a 2-alkoxy-2-heterocyclic-thioacetamide by reacting with hydrogen sulfide in the presence of a base such as an amine or by reacting with ammonium polysulfide or, alternatively, the acetamide is reacted with phosphorus pentasulfide to give the corresponding thioacetamide. The N-substituted thioacetamides may be prepared by reacting the N-unsubstituted compounds with the appropriate amine.

The lower alkyl 2-alkoxy-2-heterocyclic-acetate intermediates in procedure B may also be prepared by reacting an alkoxymethyl-heterocycle (which is an intermediate in procedure A) with a strong base such as phenyl lithium and a lower alkyl chloroformate.

Alternatively, the N-substituted 2-alkoxy-thioacetamide starting materials may be prepared by the following procedures:

a. reacting a lower alkyl 2-alkoxy-2-heterocyclic-acetate with the appropriate substituted amine and treating the resulting N-substituted 2-alkoxy-2-heterocyclic-acetamide with phosphorus pentasulfide;

b. reacting an alkoxymethyl-heterocycle with a strong base such as phenyl lithium and a N,N-di-lower alkylcarbamoyl chloride and treating the resulting N,N-di-lower allyl-2-alkoxy-2-heterocyclic-acetamide with phosphorus pentasulfide;

c. reacting an alkoxymethyl-heterocycle with a strong base such as phenyl lithium and a N,N-di-lower alkyl-thiocarbamoyl chloride.

According to procedure c, a heterocyclic-carboxaldehyde, an amine and an alkali metal cyanide are reacted, preferably in the presence of acid, to give a 2-amino-2-heterocyclic-acetonitrile which is converted to a 2-amino-2-heterocylic-thioacetamide by reacting with hydrogen sulfide in the presence of base such as an amine or by reacting with ammonium polysulfide. The corresponding N-substituted thiocetamides are prepared by reacting the N-unsubstituted compounds with the appropriate amine.

The pharmaceutically acceptable, acid addition salts of the compounds of Formula I are formed with organic and inorganic acids by methods known to the art. For example, the base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, succinate, oxalate, benzoate, methansulfonate, ethanedisulfonate, benzenesulfonate, acetate, propionate, tartrate, citrate, camphorsulfonate, hydrochloride, hydrobromide, sulfate, sulfamate, phosphate and nitrate salts.

The compounds of this invention are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

It will be apparent to one skilled in the art that the compound of this invention have an asymmetric carbon atom and thus may be present as optical isomers. The connotation of the formulas presented herein is to include all isomers, the separated isomers as well as mixtures thereof. Preferably, the optically active thiopropanamides are prepared by the use of optically active strong acids, such as camphorsulfonic acid, dibenzoyltartaric acid or phenethylsulfamic acid, to separate the optical isomers of the thiopropanamides.

The terms "lower alkyl" and "lower alkoxy" where used herein denote groups having 1–4 carbon atoms and "halogen" denotes chloro, bromo or fluoro.

The following examples are not limiting but are illustrative of the compounds of this invention and processes for their preparation.

EXAMPLE 1

2-(Chloromethyl)pyridine hydrochloride (16.3 g., 0.1 mole) is dissolved in 100 ml. of methanol. Freshly prepared sodium methoxide (5 g., 0.22 mole of sodium dissolved in 150 ml. of methanol) is added dropwise. The resulting mixture is heated at reflux for 18 hours, then fitted. The filtrate is concentrated. Water and ether are added, the aqueous phase is extracted with ether and the combined ethereal phases are washed with water and saturated aqueous sodium chloride, then dried over magnesium sulfate, concentrated and distilled to give 2-(methoxymethyl)pyridine.

Alternatively, 0.1 mole of 2-(chloromethyl)pyridine and 0.11 mole of sodium methoxide are used in the above procedure to give 2-(methoxymethyl)pyridine.

Also, 2-(methoxymethyl)pyridine is prepared by the following alternative procedure. A mixture of 10.9 g. of 2-pyridinemethanol and 2.4 g. of sodium hydride in 50 ml. of dimethylsulfoxide is warmed on a steam bath for 15 minutes, then cooled to room temperature. Methyl iodide (14.2 g.) is added then the mixture is heated at 40°C. for one hour. Water (150 ml.) is then added and the mixture is extracted with ether. The extracts are dried, concentrated and distilled to give 2-(methoxymethyl)pyridine.

2-(Methoxymethyl)pyridine (4.4 g., 0.036 mole), dissolved in 25 ml. of dry benzene, is added dropwise to 20 ml. of 2M phenyl lithium (0.04 mole) in benzene/ether with cooling. The mixture is stirred for 30 minutes, then methyl isothiocyanate (2.6 g., 0.03 mole), dissolved in 40 ml. of dry benzene, is added dropwise with cooling. The resulting solution is stirred overnight. An equal volume of water is added and the solution is cooled and made acidic with 10% hydrochloric acid. The phases are separated, the organic phase is washed with water and the combined aqueous phases are made basic to about pH 9, then extracted with chloroform. The chloroform extracts are washed with water and dried over magnesium sulfate. Filtration and removal of solvent gives a residue which is recrystallized from isopropyl ether/ethanol to give 2-methoxy-N-methyl-2-(2-pyridyl)thioacetamide, m.p. 104°–105°C.

A solution of 1.96 g. (0.01 mole) of 2-methoxy-N-methyl-2-(2-pyridyl)thioacetamide in 20 ml. of methanol is treated with 1.3 g. (0.015 mole) of morpholine and 0.45 g. (0.015 mole) of formaldehyde. The mixture is refluxed for 48 hours. The solvents are removed in vacuo. The residue is recrystallized twice from 2-propanol to give 2-methoxy-N-methyl-3-morpholino-2-(2-pyridyl)thiopropanamide, m.p. 128°–132°C.

EXAMPLE 2

By the procedure of Example 1, using in place of sodium methoxide, the following sodium alkoxides:
  sodium ethoxide
  sodium propoxide
  sodium butoxide
  sodium allyloxide
  sodium cyclopropanemethoxide
the following thioacetamides are obtained, respectively:
  2-ethoxy-N-methyl-2-(2-pyridyl)thioacetamide
  N-methyl-2-propoxy-2-(2-pyridyl)thioacetamide
  2-butoxy-N-methyl-2-(2-pyridyl)thioacetamide
  2-allyloxy-N-methyl-2-(2-pyridyl)thioacetamide
  2-cyclopropanemethoxy-N-methyl-2(-2-pyridyl)thioacetamide.

Reacting the above prepared thioacetamides with formaldehyde and morpholine by the procedure of Example 1 gives the following products, respectively:
  2-ethoxy-N-methyl-3-morpholino-2-(2-pyridyl)thiopropanamide
  N-methyl-3-morpholino-2-propoxy-2-(2-pyridyl)thiopropanamide
  2-butoxy-N-methyl-3-morpholino-2-(2-pyridyl)thiopropanamide
  2-allyloxy-N-methyl-3-morpholino-2-(2-pyridyl)thiopropanamide
  2-cyclopropanemethoxy-N-methyl-3-morpholino-2-(2-pyridyl)thiopropanamide.

EXAMPLE 3

By the procedure of Example 1, using in place of 2-(chloromethyl)pyridine, the following:
  2-(chloromethyl)pyrazine
  2-(chloromethyl)quinoline
  2-(chloromethyl)thiazole
  4-(chloromethyl)thiazole
the following thioacetamides are obtained respectively:
  2-methoxy-N-methyl-2-(2-pyrazinyl)thioacetamide
  2-methoxy-N-methyl-2-(2-quinolyl)thioacetamide
  2-methoxy-N-methyl-2-(2-thiazolyl)thioacetamide
  2-methoxy-N-methyl-2-(4-thiazolyl)thioacetamide.

The above prepared thioacetamides are reacted with formaldehyde and morpholine by the procedure of Example 1 to give the following products, respectively:
  2-methoxy-N-methyl-3-morpholino-2-(2-pyrazinyl)thiopropanamide
  2-methoxy-N-methyl-3-morpholino-2-(2-quinolyl)thiopropanamide
  2-methoxy-N-methyl-3-morpholino-2-(2-thiazolyl)thiopropanamide
  2-methoxy-N-methyl-3-morpholino-2-(4-thiazolyl)thiopropanamide.

EXAMPLE 4

A mixture of 6.3 g. of 2-pyrrolemethanol and 25 ml. of thionyl chloride is heated on a steam bath for 4 hours. The mixture is then concentrated under reduced pressure and the residue is dissolved in water, basified with 5% aqueous sodium bicarbonate solution and extracted with ether. The extracts are dried, concentrated and distilled to give 2-(chloromethyl)pyrrole.

Using 2-(chloromethyl)pyrrole in place of 2-(chloromethyl)pyridine in the procedure of Example 1 gives 2-methoxy-N-methyl-3-morpholino-2-(2-pyrrolyl)thiopropanamide.

In the same manner, converting 2-pyrimidinemethanol to 2-(chloromethyl)pyrimidine and using 2-(chloromethyl)pyrimidine in the procedure of Example 1, the product is 2-methoxy-N-methyl-3-morpholino-2-(2-pyrimidyl)thiopropanamide.

EXAMPLE 5

4-Pyrimidinecarboxylic acid is reduced using lithium aluminum hydride in ether to give 4-pyrimidinemethanol.

4-Pyrimidinemethanol is converted to 4-(chloromethyl)pyrimidine by the procedure of Example 4.

Using 4-(chloromethyl)pyrimidine in the procedure of Example 1, the product is 2-methoxy-N-methyl-3-morpholino-2-(4-pyrimidyl)thiopropanamide.

EXAMPLE 6

To a solution containing 12.1 g. (0.08 mole) of methyl 2-(2-pyridyl)acetate in 120 ml. of carbon tetrachloride is added 14.8 g. (0.084 mole) of N-bromosuccinimide and 0.3 g. of dibenzoylperoxide. The solution is irradiated by means of a sun-lamp source until essentially all the solid (succinimide) has risen to the top (about 10–15 minutes).

The solution is filtered and the solvent removed under reduced pressure and without heat to give methyl 2-bromo-2-(2-pyridyl)acetate.

The above prepared 2-bromo compound is dissolved in 100 ml. of dry methanol and freshly prepared sodium methoxide (0.09 mole) in 100 ml. of dry methanol is added dropwise. Then the mixture is stirred for 3 hours at room temperature. The solvent is removed under reduced pressure and without heat to give methyl 2-methoxy-2-(2-pyridyl)acetate.

The above prepared 2-methoxy compound is dissolved in 65 ml. of concentrated ammonium hydroxide and the solution is stirred for 6.5 hours. The mixture is then concentrated, dissolved in chloroform and extracted twice with brine. The organic phase is dried over magnesium sulfate and filtered and solvent is removed under reduced pressure to give 2-methoxy-2-(2-pyridyl)-acetamide.

To 20 ml. of dry 1,2-dichloroethane containing 2.0 g. of sodium chloride is added 3.22 g. of 2-methoxy-2-(2-pyridyl)acetamide. After stirring at room temperature for 15 minutes, 1.7 ml. of phosphorus oxychloride is added. The solution is refluxed for 18 hours. The solution is then cooled and made basic with 10% aqueous sodium hydroxide solution. The aqueous phase is extracted three times with chloroform and the combined chloroform extracts are washed three times with water and once with brine and dried over magnesium sulfate. Filtration, removal of solvent and distillation in vacuo gives 2-methoxy-2-(2-pyridyl)acetonitrile, b.p. 72°–76°C./0.2 mm.

In 125 ml. of dry pyridine containing 4 ml. of triethylamine is dissolved 2.65 g. (0.018 mole) of 2-methoxy-2-(2-pyridyl)acetonitrile. Hydrogen sulfide is bubbled through the solution for 5.5 hours. The solvent is evaporated under reduced pressure and chloroform is added to the residue. The mixture is allowed to stand at −20°C. for 18 hours. The precipitate is filtered off and recrystallized from isopropanol to give 2-methoxy-2-(2-pyridyl)thioacetamide, m.p. 157°–159°C.

A solution of 9.1 g. of 2-methoxy-2-(2-pyridyl)-thioacetamide in a 40% aqueous solution of cyclopropylamine is heated at reflux for 45 minutes. The mixture is cooled and 30 ml. of water is added. The mixture is extracted with chloroform and the extracts are dried over magnesium sulfate and concentrated to give after recrystallizing the residue, N-cyclopropyl-2-methoxy-2-(2-pyridyl)thioacetamide.

By the procedure of Example 1, reacting the above prepared thioacetamide with formaldehyde and morpholine gives N-cyclopropyl-2-methoxy-3-morpholine-2-(2-pyridyl)thiopropanamide.

By the same procedure, using the following cycloalkylamines:
cyclobutylamine
cyclopentylamine
cyclohexylamine
the products are, respectively:
N-cyclobutyl-2-methoxy-3-morpholino-2-(2-pyridyl)thiopropanamide
N-cyclopentyl-2-methoxy-3-morpholino-2-(2-pyridyl)thiopropanamide
N-cyclohexyl-2-methoxy-3-morpholino-2-(2-pyridyl)thiopropanamide.

EXAMPLE 7

Using cyclopropanemethyl isothiocyanate in place of methyl isothiocyanate in the procedure of Example 1 gives N-cyclopropanemethyl-2-methoxy-3-morpholine-2-(2-pyridyl)thiopropanamide.

EXAMPLE 8

Alternatively, N-cyclopropanemethyl-2-methoxy-2-(2-pyridyl)thioacetamide is prepared by the following procedure.

A solution of 6.0 g. of cyclopropanemethylamine hydrochloride and 4.7 g. of sodium bicarbonate in 75 ml. of water is added to 5.4 g. of 2-methoxy-2-(2-pyridyl)-thioacetamide. The reaction mixture is heated on a steam bath with stirring for 4 hours. The mixture is then cooled and 25 ml. of water is added. The reaction mixture is extracted three times with chloroform. The chloroform extracts are combined, dried over magnesium sulfate and then evaporated. The residue is purified by "dry-column" chromatography on silica gel, using ethyl acetate as solvent. Recrystallization gives N-cyclopropanemethyl-2-methoxy-2-methoxy-(2-pyridyl)thioacetamide.

Reacting the above prepared thioacetamide with formaldehyde and morpholine by the procedure of Example 1 gives N-cyclopropanemethyl-2-methoxy-3-morpholino-2-(2-pyridyl)thiopropanamide.

Similarly, using in place of cyclopropanemethylamine hydrochloride, the following:
cyclobutanemethylamine hydrochloride
cyclopentanemethylamine hydrochloride
cyclohexanemethylamine hydrochloride
the products are, respectively:
N-cyclobutanemethyl-2-methoxy-3-morpholino-2-(2-pyridyl)thiopropanamide
N-cyclopentanemethyl -2-methoxy-3-morpholino-2-(2-pyridyl)thiopropanamide
N-cyclohexanemethyl-2-methoxy-3-morpholino-2-(2-pyridyl)thiopropanamide.

EXAMPLE 9

By the procedure of Example 6, using in place of methyl 2-(2-pyridyl)acetate, the following:

methyl 2-(2-pyrrolyl)acetate
ethyl 2-(2-quinolyl)acetate
ethyl 2-(4-thiazolyl)acetate
ethyl 2-(4-methyl-2-thiazolyl)acetate
ethyl 2-(3-methyl-2-pyrazinyl)acetate
the products are, respectively:
N-cyclopropyl-2-methoxy-3-morpholino-2-(2-pyrrolyl)-thiopropanamide
N-cyclopropyl-2-methoxy-3-morpholino-2-(2-quinolyl)-thiopropanamide
N-cyclopropyl-2-methoxy-3-morpholino-2-(4-thiazolyl)-thiopropanamide
N-cyclopropyl-2-methoxy-3-morpholino-2-(4-methyl-2-thiazolyl)thiopropanamide
N-cyclopropyl-2-methoxy-3-morpholino-2-(3-methyl-2-pyrazinyl)-thiopropanamide.

Similarly, the corresponding N-cyclobutyl, N-cyclopentyl and N-cyclohexyl compounds are prepared.

EXAMPLE 10

By the procedure of Example 8, using the appropriate 2-alkoxy-2-heterocyclic-thioacetamide, prepared from the corresponding lower alkyl heterocyclic-acetate by the procedure of Example 6, the following products are obtained:
N-cyclopropanemethyl-2-methoxy-3-morpholino-2-(2-pyrrolyl)thiopropanamide
N-cyclopropanemethyl-2-methoxy-3-morpholino-2-(2-quinolyl)thiopropanamide
N-cyclopropanemethyl-2-methoxy-3-morpholino-2-(4-thiazolyl)thiopropanamide.

EXAMPLE 11

2-(Methoxymethyl)pyridine (1.85 g., 0.015 mole) in 15 ml. of dry benzene is added dropwise to a chilled solution of phenyl lithium (8.1 ml. of 2.1 molar solution, 0.017 mole) in 15 ml. of dry benzene. After the addition is complete, the mixture is stirred at 0°C. for one hour. Phenyl isothiocyanate (2.03 g., 0.015 mole) in 15 ml. of dry benzene is added dropwise and the mixture is allowed to come to room temperature gradually, then the mixture is stirred overnight. The mixture is diluted with 50 ml. of water and acidified with dilute hydrochloric acid. The layers are separated and the organic layer is washed several times with water. The aqueous layers are combined, basified with dilute aqueous sodium hydroxide solution and extracted several times with chloroform. The chloroform extracts are combined, washed once with brine and dried over magnesium sulfate. The solvent is removed under reduced pressure to give an oil which is placed on a silica gel "dry-column", eluting with ethyl acetate to give, after cooling and recrystallizing from ethyl acetate/hexane, 2-methoxy-N-phenyl-2-(2-pyridyl)thioacetamide, m.p. 97°–98.5°C.

Reacting the above prepared thioacetamide with formaldehyde and morpholine gives 2-methoxy-3-morpholino-N-phenyl-2-(2-pyridyl)thiopropanamide.

EXAMPLE 12

In the procedure of Example 1, using the following in place of methyl isothiocyanate:
ethyl isothiocyanate
propyl isothiocyanate
butyl isothiocyanate
the products are, respectively:
N-ethyl-2-methoxy-3-morpholino-2-(2-pyridyl)thiopropanamide
2-methoxy-3-morpholino-N-propyl-2-(2-pyridyl)thiopropanamide
N-butyl-2-methoxy-3-morpholino-2-(2-pyridyl)thiopropanamide.

EXAMPLE 13

A mixture of 18.1 g. of methyl 2-methoxy-2-(2-pyridyl)acetate and 10 g. of dimethylamine in ethanol is stirred at room temperature for 26 hours. The mixture is concentrated, dissolved in chloroform and extracted with brine. The organic phase is dried over magnesium sulfate and filtered and the solvent is removed under reduced pressure to give 2-methoxy-N,N-dimethyl-2-(2-pyridyl)acetamide.

Alternatively, 2-methoxy-N,N-dimethyl-2-(2-pyridyl)acetamide is prepared by the following procedure. 2-Methoxy-2-(2-pyridyl)acetyl chloride hydrochloride, 22 g., [prepared by reacting 2-methoxy-2-(2-pyridyl)acetic acid in benzene with thionyl chloride] in 100 ml. of chloroform is added dropwise and with cooling to 50 g. of dimethylamine in 100 ml. of chloroform. The mixture is stirred for 4 hours, then 50 ml. of 5% aqueous sodium hydroxide is added and the chloroform solution is dried and concentrated to give 2-methoxy-N,N-dimethyl-2-(2-pyridyl)acetamide.

Phosphorus pentasulfide (4 g.) is added to 9.7 g. of 2-methoxy-N,N-dimethyl-2-(2-pyridyl)acetamide in 25 ml. of pyridine. The mixture is heated on a steam bath for 2 hours, then 250 ml. of water and 10 ml. of 5% aqueous sodium hydroxide solution are added. The mixture is extracted with chloroform and the extracts are dried and concentrated and the residue is recrystallized to give 2-methoxy-N,N-dimethyl-2-(2-pyridyl)-thioacetamide.

By the procedure of Example 1, reacting the above prepared thioacetamide with formaldehyde and morpholine gives 2-methoxy-N,N-dimethyl-3-morpholino-2-(2-pyridyl)-thiopropanamide.

EXAMPLE 14

Alternatively, 2-methoxy-N,N-dimethyl-2-(2-pyridyl)thioacetamide is prepared by the following procedures.

To 0.10 mole of phenyl lithium in 100 ml. of benzene/ether at 0°C. is added dropwise 10.6 g. (0.084 mole) of 2-(methoxymethyl)pyridine dissolved in 75 ml. of benzene. To this mixture is added dropwise 10.0 g. (0.081 mole) of N,N-dimethylthiocarbamoyl chloride in 100 ml. of benzene. The resulting mixture is stirred at room temperature overnight, then poured into 100 ml. of water and acidified. The organic phase is extracted once with dilute aqueous acid. The combined aqueous phases are extracted twice with ether, then made basic to about pH 10 and extracted three times with chloroform. The combined chloroform extracts are dried over magnesium sulfate and the solvent is removed by evaporation. The residue is chromatographed, then distilled in vacuo to give 2-methoxy-N,N-dimethyl-2-(2-pyridyl)thioacetamide.

Alternatively, using N,N-dimethylcarbamoyl chloride in the above procedure gives 2-methoxy-N,N-dimethyl-2-(2-pyridyl)acetamide which is converted to the thioacetamide by reaction with phosphorus pentasulfide by the procedure described in Example 13.

Also, by the procedure of Example 1, reacting 2-methoxy-N,N-dimethyl-2-(2-pyridyl)thioacetamide with formaldehyde and morpholine, the product is 2-methoxy-N,N-dimethyl-3-morpholino-2-(2-pyridyl)- thiopropanamide.

EXAMPLE 15

Using the following N,N-di-lower alkylthiocarbamyl chloride compounds in the procedure of Example 14:
N,N-diethylthiocarbamoyl chloride
N,N-dipropylthiocarbamoyl chloride
N,N-dibutylthiocarbamoyl chloride
the products are, respectively:
N,N-diethyl-2-methoxy-3-morpholino-2-(2-pyridyl)-thiopropanamide
2-methoxy-N,N-dipropyl-3-morpholino-2-(2-pyridyl)thiopropanamide
N,N-dibutyl-2-methoxy-3-morpholino-2-(2-pyridyl)-thiopropanamide.

EXAMPLE 16

A solution of 9.95 g. (0.081 mole) of 2-(methoxymethyl)pyridine in 80 ml. of dry benzene is added dropwise to a chilled solution of 40 ml. (0.084 mole) of phenyl lithium in 80 ml. of dry benzene. The mixture is stirred at 0°C. for 1 hour after the addition is complete. Then 8.02 g. of allyl isothiocyanate in 50 ml. of benzene is added dropwise and the mixture is allowed to come to room temperature gradually. The mixture is the diluted with 500 ml. of water and acidified with 10% hydrochloric acid. The layers are separated and the organic layer is washed several times with water. The aqueous layers are combined, neutralized with 10% aqueous sodium hydroxide solution and then brought to pH 9 with 5% aqueous sodium bicarbonate solution, then extracted with chloroform. The chloroform extracts are washed once with brine and dried over magnesium sulfate. The solvent is removed and the residue is chromatographed on a silica gel column, eluting with ethyl acetate. The fractions containing the product are combined and evaporated and the residue is recrystallized from ethyl acetate/hexane to give N-allyl-2-methoxy-2-(2-pyridyl)thioacetamide, m.p. 59.5°–60°C.

Reacting N-allyl-2-methoxy-2-(2-pyridyl)thioacetamide with formaldehyde and morpholine by the procedure of Example 1 gives N-allyl-2-methoxy-3-morpholino-2-(2-pyridyl)thiopropanamide.

EXAMPLE 17

To a solution containing 12.1 g. (0.08 mole) of methyl 2-(2-pyridyl)acetate in 120 ml. of carbon tetrachloride is added 14.8 g. (0.084 mole) of N-bromosuccinimide and 0.3 g. of dibenzoylperoxide. The solution is irradiated by means of a sun-lamp source until essentially all the solid (succinimide) has risen to the top (about 10–15 minutes).

The solution is filtered and the solvent removed under reduced pressure and without heat to give methyl 2-bromo-2-(2-pyridyl)acetate.

The above prepared 2-bromo compound is dissolved in 100 ml. of dry methanol and freshly prepared sodium methoxide (0.09 mole) in 100 ml. of dry methanol is added dropwise. Then the mixture is stirred for 3 hours at room temperature. The solvent is removed under reduced pressure and without heat to give methyl 2-methoxy-2-(2-pyridyl)acetate.

The above prepared 2-methoxy compound is dissolved in 65 ml. of concentrated ammonium hydroxide and the solution is stirred for 6.5 hours. The mixture is then concentrated, dissolved in chloroform and extracted twice with brine. The organic phase is dried over magnesium sulfate and filtered and solvent is removed under reduced pressure to give 2-methoxy-2-(2-pyridyl)acetamide.

To 20 ml. of dry 1,2-dichloroethane containing 2.0 g. of sodium chloride is added 3.32 g. of 2-methoxy-2-(2-pyridyl)acetamide. After stirring at room temperature for 15 minutes, 1.7 ml. of phosphorus oxychloride is added. The solution is refluxed for 18 hours. The solution is then cooled and made basic with 10% aqueous sodium hydroxide solution. The aqueous phase is extracted three times with chloroform and the combined chloroform extracts are washed three times with water and once with brine and dried over magnesium sulfate. Filtration, removal of solvent and distillation in vacuo gives 2-methoxy-2-(2-pyridyl)acetonitrile, b.p. 72°–76°C./0.2 mm.

In 125 ml. of dry pyridine containing 4 ml. of triethylamine is dissolved 2.65 g. (0.018 mole) of 2-methoxy-2-(2-pyridyl)acetonitrile. Hydrogen sulfide is bubbled through the solution for 5.5 hours. The solvent is evaporated under reduced pressure and chloroform is added to the residue. The mixture is allowed to stand at −20°C. for 18 hours. The precipitate is filtered off and recrystallized from isopropanol to give 2-methoxy-2-(2-pyridyl)thioacetamide, m.p. 157°–159°C.

To 4.4 g. (0.026 mole) of 2-methoxy-2-(2-pyridyl)-thioacetamide in 20 ml. of water at 0°C. is added 2.9 g. (0.053 mole) of propargylamine with stirring and the resulting suspension is allowed to stand overnight at 5°C. Ethanol (5 ml.) is added and the mixture is stirred for 5 hours, then extracted with dichloromethane. The extracts are dried and concentrated. The residue is chromatographed on a silica gel "dry-column", using 1:10 ethyl acetate/ether as the eluant. The product fraction is treated with charcoal, filtered, concentrated and the residue is recrystallized from benzene/ligroin to given 2-methoxy-N-propargyl-2-(2-pyridyl)thioacetamide.

The above prepared thioacetamide is reacted with formaldehyde and morpholine by the procedure of Example 1 to give 2-methoxy-3-morpholino-N-propargyl-2-(2-pyridyl)thiopropanamide.

By the same procedure, using in place of propargylamine, the following amines:
1-methylallylamine
2-ethylallylamine
2-butenylamine
4-methyl-2-pentenylamine
2-butynylamine
2-pentynylamine
1-ethyl-1-methyl-2-propynylamine
the products are, respectively:
2-methoxy-N-(1-methylallyl)-3-morpholino-2-(2-pyridyl)thiopropanamide
N-(2-ethylallyl)-2-methoxy-3-morpholino-2-(2-pyridyl)thiopropanamide
N-(2-butenyl)-2-methoxy-3-morpholino-2-(2-pyridyl)-thiopropanamide
2-methoxy-N-(4-methyl-2-pentenyl)-3-morpholino-2-(2-pyridyl)thiopropanamide
N-(2-butynyl)-2-methoxy-3-morpholino-2-(2-pyridyl)-thiopropanamide
2-methoxy-3-morpholino-N-(2-pentynyl)-2-(2-pyridyl)thiopropanamide
N-(1-ethyl-1-methyl-2-propynyl)-2-methoxy-3-morpholino-2-(2-pyridyl)thiopropanamide.

EXAMPLE 18

Using piperidine in place of morpholine in the procedure of Example 1, the product is 2-methoxy-N-methyl-3-piperidino-2-(2-pyridyl)thiopropanamide.

Similarly, using pyrrolidine, the product is 2-methoxy-N-methyl-3-pyrrolidino-2-(2-pyridyl)thiopropanamide.

By the same procedure, using 1-methylpiperazine, the product is 2-methoxy-N-methyl-3-(4-methylpiperazino)-2-(2-pyridyl)thiopropanamide.

EXAMPLE 19

Using diethylamine in place of morpholine in the procedure of Example 1, the product is 3-diethylamino-2-methoxy-N-methyl-2-(2-pyridyl)thiopropanamide.

Similarly, using the following amines:
dimethylamine
dipropylamine
dibutylamine
the products are, respectively:
3-dimethylamino-2-methoxy-N-methyl-2-(2-pyridyl)thiopropanamide
3-dipropylamino-2-methoxy-N-methyl-2-(2-pyridyl)thiopropanamide.
3-dibutylamino-2-methoxy-N-methyl-2-(2-pyridyl)thiopropanamide.

EXAMPLE 20

By the procedure of Example 1, using 2-(chloromethyl)quinoline in place of 2-(chloromethyl)pyridine, 2-methoxy-N-methyl-2-(2-quinolyl)thioacetamide is prepared. Reacting this thioacetamide with formaldehyde and diethylamine gives 3-diethylamino-2-methoxy-N-methyl-2-(2-quinolyl)thiopropanamide.

Similarly, using in place of diethylamine the following:
piperidine
pyrrolidine
1-methylpiperazine
the products are, respectively:
2-methoxy-N-methyl-3-piperidino-2-(2-quinolyl)thiopropanamide
2-methoxy-N-methyl-3-pyrrolidino-2-(2-quinolyl)thiopropanamide
2-methoxy-N-methyl-3-(4-methylpiperazino)-2-(2-quinolyl)thiopropanamide.

EXAMPLE 21

One gram of 2-methoxy-N-methyl-3-morpholino-2-(2-pyridyl)thiopropanamide in ether is added to ethereal hydrogen chloride. The resulting precipitate is filtered off and recrystallized from ethanol/ether to give 2-methoxy-N-methyl-3-morpholino-2-(2-pyridyl)thiopropanamide hydrochloride.

By the same procedure, the hydrochloride salt of 2-methoxy-N-methyl-3-morpholino-2-(2-quinolyl)thiopropanamide is prepared.

EXAMPLE 22

Two grams of 2-methoxy-N-methyl-3-morpholino-2-(2-pyridyl)thiopropanamide in ethanol is treated with an equilmolar amount of maleic acid in ethanol to give, after removing the solvent under reduced pressure, 2-methoxy-N-methyl-3-morpholino-2-(2-pyridyl)thiopropanamide maleate.

By the same procedure, using citric acid, the citrate salt of 2-methoxy-N-methyl-3-morpholino-2-(2-pyridyl)thiopropanamide is prepared.

EXAMPLE 23

To cold 2-pyridinecarboxaldehyde (21.4 g., 0.2 mole) is added dimethylamine (22.5 g. of a 40% aqueous solution, 0.2 mole) and the solution is neutralized with concentrated hydrochloric acid. To the stirred neutralized solution is added 14.4 g. (0.22 mole) of potassium cyanide. The mixture is stirred overnight, then diluted with water, transferred to a separatory funnel and repeatedly extracted with chloroform. The combined chloroform extracts are washed three times with water, once with brine and dried over magnesium sulfate. The mixture is filtered, the solvent is removed under reduced pressure and methanol is added to the residue. The mixture is allowed to stand at −20°C. for 18 hours, then filtered. The filtrate is concentrated and distilled in vacuo to give 2-dimethylamino-2-(2-pyridyl)acetonitrile.

2-Dimethylamino-2-(2-pyridyl)acetonitrile (11.4 g., 0.07 m.) is dissolved in 200 ml. of dry pyridine containing 5 ml. of anhydrous triethylamine. Hydrogen sulfide is bubbled into the stirred solution for 7 hours and the solution is then stirred for 17 hours. This procedure is repeated for 5 days. Then the mixture is stirred for an additional 48 hours. The solvent is then removed under reduced pressure and the residue is recrystallized from ethanol to give 2-dimethylamino-2-(2-pyridyl)thioacetamide, m.p. 130°–133°C. (dec.).

A mixture of 7.5 g. of 2-dimethylamino-2-(2-pyridyl)thioacetamide and 15 ml. of 30% aqueous methylamine is heated for 30 minutes, then cooled and 25 ml. of 5% aqueous sodium carbonate solution is added. The solution is extracted with chloroform, the organic solution is dried and concentrated and the residue is recrystallized to give 2-dimethylamino-N-methyl-2-(2-pyridyl)thioacetamide.

A mixture of 19.5 g. of 2-dimethylamino-N-methyl-2-(2-pyridyl)thioacetamide in 200 ml. of methanol, 13 g. of morpholine and 4.5 g. of formaldehyde is heated at reflux for 48 hours. The mixture is concentrated in vacuo and the residue is recrystallized from isopropyl ether to give 2-dimethylamino-N-methyl-3-morpholino-2-(2-pyridyl)thiopropanamide.

EXAMPLE 24

In the procedure of Example 23, using 2-dimethylamino-2-(2-quinolyl)acetonitrile in place of 2-dimethylamino-2-(2-pyridyl)acetonitrile, the product is 2-dimethylamino-N-methyl-3-morpholino-2-(2-quinolyl)thiopropanamide.

EXAMPLE 25

By the procedure of Example 23, using in place of 2-dimethylamino-2-(2-pyridyl)acetonitrile the following substituted acetonitriles:
2-diethylamino-2-(2-pyridyl)acetonitrile
2-pyrrolidino-2-(2-pyridyl)acetonitrile
2-piperidino-2-(2-pyridyl)acetonitrile
2-dimethylamino-2-(6-methyl-2-pyridyl)acetonitrile
the products are, respectively:
2-diethylamino-N-methyl-3-morpholino-2-(2-pyridyl)-thiopropanamide
N-methyl-3-morpholino-2-pyrrolidino-2-(2-pyridyl)-thiopropanamide N-methyl-3-morpholino-2-piperidino-2-(2-pyridyl)-thiopropanamide 2-dimethylamino-N-methyl-3-morpholino-2-(6-methyl-2-pyridyl)thiopropanamide.

EXAMPLE 26

By the procedure of Example 23, 2-pyridinecarboxaldehyde is reacted with N-methylpiperazine and potassium cyanide to give 2-(4-methylpiperazino)-2-(2-pyridyl)acetonitrile.

Hydrogen sulfide is bubbled into a stirred solution of 12.0 g. of 2-(4-methylpiperazino)-2-(2-pyridyl)acetonitrile in 200 ml. of dry pyridine and 5 ml. of anhydrous triethylamine for 7 hours. The mixture is then stirred for 17 hours. This procedure is repeated for 5 days and the mixture is worked up as in Example 23 to give 2-(4-methylpiperazino)-2-(2-pyridyl)-thioacetamide.

The above prepared thioacetamide is reacted with methylamine and the resulting N-methyl compound is reacted with formaldehyde and morpholine by the procedure of Example 23 to give N-methyl-2-(4-methylpiperazino)-3-morpholino-2-(2-pyridyl)thiopropanamide.

Similarly, using in place of N-methylpiperazine the following lower alkylpiperazines:
N-ethylpiperazine
N-propylpiperazine
N-butylpiperazine
the products are, respectively:
2-(4-ethylpiperazino)-N-methyl-3-morpholino-2-(2-pyridyl)thiopropanamide
N-methyl-3-morpholino-2-(4-propylpiperazino)-2-(2-pyridyl)thiopropanamide
2-(4-butylpiperazino)-N-methyl-3-morpholino-2-(2-pyridyl)thiopropanamide.

EXAMPLE 27

By the procedure of Example 23, using dipropylamine in place of dimethylamine the product is 2-dipropylamino-N-methyl-3-morpholino-(2-pyridyl)thiopropanamide.

Similarly, using dibutylamine, the product is 2-dibutylamino-N-methyl-3-morpholino-2-(2-pyridyl)-thiopropanamide.

EXAMPLE 28

By the procedure of Example 23, using in place of 2-pyridinecarboxaldehyde, the following carboxaldehydes:
2-pyrimidinecarboxaldehyde
2-pyrrolecarboxaldehyde
2-pyrazinecarboxaldehyde
4-pyrimidinecarboxaldehyde
2-thiazolecarboxaldehyde
4-thiazolecarboxaldehyde
the products are, respectively:
2-dimethylamino-N-methyl-3-morpholino-2-(2-pyrimidyl)thiopropanamide
2-dimethylamino-N-methyl-3-morpholino-2-(2-pyrrolyl)thiopropanamide
2-dimethylamino-N-methyl-3-morpholino-2-(2-pyrazinyl)thiopropanamide
2-dimethylamino-N-methyl-3-morpholino-2-(4-pyrimidyl)thiopropanamide
2-dimethylamino-N-methyl-3-morpholino-2-(2-thiazolyl)thiopropanamide 2-dimethylamino-N-methyl-3-morpholino-2-(4-thiazolyl)thiopropanamide.

EXAMPLE 29

A mixture of 2-dimethylamino-2-(2-pyridyl)thioacetamide and 40% aqueous solution of cyclopropylamine is heated at reflux for 45 minutes. The mixture is cooled and water is added. The mixture is then extracted with chloroform and the extracts are dried, concentrated and the residue is recrystallized to give N-cyclopropyl-2-dimethylamino-2-(2-pyridyl)thioacetamide.

The above prepared thioacetamide is reacted with formaldehyde and morpholine to give N-cyclopropyl-2-dimethylamino-3-morpholino-2-(2-pyridyl)thiopropanamide.

By the same procedure, using 2-piperidino-2-(2-pyridyl)thioacetamide, the product is N-cyclopropyl-3-morpholino-2-piperidino-2-(2-pyridyl)thiopropanamide.

EXAMPLE 30

To 5.65 g. of 2-dimethylamino-2-(2-pyridyl)thioacetamide is added 6.02 g. of cyclopropanemethylamine hydrochloride and 4.71 g. of sodium bicarbonate which are dissolved in 75 ml. of water and the resulting mixture is heated with stirring on a steam bath for 4 hours. The mixture is cooled and 25 ml. of water is added. The mixture is extracted with chloroform, dried and then concentrated. The residue is chromatographed and recrystallized to give N-cyclopropanemethyl-2-dimethylamino-2-(2-pyridyl)thioacetamide.

Reacting the above prepared thioacetamide with formaldehyde and piperidine by the procedure of Example 1 gives N-cyclopropanemethyl-2-dimethylamino-3-piperidino-2-(2-pyridyl)thiopropanamide.

By the same procedure, using cyclopentanemethylene hydrochloride, the product is N-cyclopentanemethyl-2-dimethylamino-3-piperidino-2-(2-pyridyl)thiopropanamide.

What is claimed is:

1. A compound of the formula:

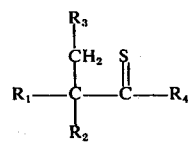

in which:
R$_1$ is 2-pyrimidyl, 4-pyrimidyl or 2-pyrazinyl;
R$_2$ is lower alkoxy, allyloxy, cyclopropanemethoxy, di-lower alkylamino, piperidino, pyrrolidino, N-lower alkylpiperazino or morpholino;
R$_3$ is di-lower alkylamino, piperidino, pyrrolidino, N-lower alkylpiperazino or morpholino;
R$_4$ is NH-(lower alkyl), N(lower alkyl)$_2$, NH-phenyl, NH—(CH$_2$)$_n$-cycloalkyl, said cycloalkyl having 3–6 carbon atoms, or NH—R$_5$;
$n$ is 0 or 1 and
R$_5$ is an allyl or propargyl group optionally substituted by methyl or ethyl groups, said R$_5$ having 3–6 carbon atoms
or a pharmaceutically acceptable acid addition salt thereof.

2. A compound of claim 1 in which R$_3$ is morpholino.

3. A compound of claim 1 in which $R_2$ is lower alkoxy.

4. A compound of claim 1, said compound being 2-methoxy-N-methyl-3-morpholino-2-(2-pyrazinyl)thiopropanamide.

5. A compound of claim 1, said compound being 2-methoxy-N-methyl-3-morpholino-2-(2-pyrimidyl)thiopropanamide.

6. A compound of claim 1, said compound being 2-methoxy-N-methyl-3-morpholino-2-(4-pyrimidyl)thiopropanamide.

* * * * *

UNITED STATES PATENT AND TRADEMARK OFFICE
CERTIFICATE OF CORRECTION

PATENT NO. : 3,948,892
DATED : April 6, 1976
INVENTOR(S) : Bernard Loev

It is certified that error appears in the above–identified patent and that said Letters Patent are hereby corrected as shown below:

Column 2, line 7, "an" should read -- on -- .

Column 2, line 51, "-2-hydroxylamine" should read
-- -2-hydroxyethylamine -- .

Column 5, line 28, "fitted" should read -- filtered -- .

Column 7, line 48, "3.22 g." should read -- 3.32 g. -- .

Column 8, line 47, "-2-methoxy-2-methoxy-" should read
-- -2-methoxy-2- -- .

Signed and Sealed this twenty-second Day of June 1976

[SEAL]

Attest:

RUTH C. MASON
Attesting Officer

C. MARSHALL DANN
Commissioner of Patents and Trademarks